United States Patent
Jia et al.

(10) Patent No.: US 8,110,555 B2
(45) Date of Patent: *Feb. 7, 2012

(54) 7-HYDROXY CHROMONES AS POTENT ANTIOXIDANTS

(75) Inventors: Qi Jia, Olympia, WA (US); Thomas M. Farrow, Denver, CO (US)

(73) Assignee: Unigen, Inc., Lacey, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/721,371

(22) Filed: Mar. 10, 2010

(65) Prior Publication Data

US 2010/0168223 A1    Jul. 1, 2010

Related U.S. Application Data

(60) Continuation of application No. 11/085,896, filed on Mar. 21, 2005, now Pat. No. 7,678,772, which is a division of application No. 10/138,932, filed on May 3, 2002, now Pat. No. 6,884,783.

(51) Int. Cl.
 A01N 43/04  (2006.01)
 A01N 43/00  (2006.01)
 A61K 31/70  (2006.01)
 A61K 31/33  (2006.01)

(52) U.S. Cl. .......... 514/23; 514/183; 514/449; 514/451; 514/453; 514/456

(58) Field of Classification Search .................. None
See application file for complete search history.

(56) References Cited

U.S. PATENT DOCUMENTS

| | | | |
|---|---|---|---|
| 4,598,069 | A | 7/1986 | Hikino et al. |
| 4,725,438 | A | 2/1988 | Leazer |
| 4,851,224 | A | 7/1989 | McAnalley |
| 5,106,616 | A | 4/1992 | McAnalley et al. |
| 5,118,673 | A | 6/1992 | Carpenter et al. |
| 5,308,838 | A | 5/1994 | McAnalley et al. |
| 5,468,737 | A | 11/1995 | McAnalley et al. |
| 5,503,825 | A | 4/1996 | Lane |
| 5,587,364 | A | 12/1996 | McAnalley et al. |
| 5,627,204 | A | 5/1997 | Igarashi et al. |
| 5,703,060 | A | 12/1997 | McAnalley et al. |
| 5,773,425 | A | 6/1998 | McAnalley et al. |
| 5,780,453 | A | 7/1998 | McAnalley et al. |
| 5,888,984 | A | 3/1999 | Brown |
| 5,939,395 | A | 8/1999 | Yu et al. |
| 6,083,976 | A | 7/2000 | Padmapriya et al. |
| 6,123,959 | A | 9/2000 | Jones et al. |
| 6,133,305 | A | 10/2000 | Tang et al. |
| 6,306,383 | B1 | 10/2001 | Crandall et al. |
| 6,451,357 | B1 | 9/2002 | Farrow |
| 6,780,440 | B2 | 8/2004 | Naguib |
| 6,884,783 | B2 * | 4/2005 | Jia et al. ............ 514/23 |
| 7,678,772 | B2 * | 3/2010 | Jia et al. ............ 514/23 |
| 2008/0166438 | A1 | 7/2008 | Zhao et al. |

FOREIGN PATENT DOCUMENTS

| | | |
|---|---|---|
| CN | 1575803 | 2/2005 |
| CN | 1861169 A | 11/2006 |
| JP | 10 101541 A | 4/1998 |
| JP | 10140179 A | 5/1998 |
| JP | 2003 286185 | 10/2003 |
| KR | 2002 0078202 | 10/2002 |
| SI | 20 073 A | 4/2000 |
| WO | WO 95/05169 | 2/1995 |
| WO | WO 95/23604 | 9/1995 |
| WO | WO 96/40182 | 12/1996 |
| WO | WO 01/30342 | 5/2001 |
| WO | WO 2004/037193 | 5/2004 |
| WO | WO 2004/066912 | 8/2004 |
| WO | WO 2006/024545 | 3/2006 |

OTHER PUBLICATIONS

Office Action sent on May 4, 2009 by U.S. Appl. No. 11/085,896.
International Search Report sent on Jul. 28, 2003 by ISA for PCT/US03/13935.
Rajasekaran et al. (2006) Clin Exp Pharmacol Physiol. 33(3):232-237, "Beneficial Effects of *Aloe vera* Leaf Gel Extract on Lipid Profile Status in Rats with Streptozotocin Diabetes".
Jong-Anurakkun et al. (2008) Fitoterapria 79:456-457, "α-Glucosidase inhibitor from Chinese aloes".
Ajabnoor (1990) J. Ethnopharmacol 28:215-220, "Effect of Aloes on Blood Glucose Levels in Normal and Alloxan Diabetic Mice".
Alves et al. (1999) Journal of Molecular Structure (Theochem) 491:123-131, "A Quantum Chemical and Statistical Study of Flavonoid Compounds with Anti-HIV Activity".
Annual Drug Data Report (1991) 13(7):583, "Platelet Antaggregatory Agents—RC-3911" (Abstract).
Annual Drug Data Report (1999) 21(9):770, "Psychopharmacologic Drugs—Antipsychotic Drugs—278844" (Abstract).
Blommaart et al. (1997) Eur. J. Biochem 243:240-246, "The phosphatidylinositol 3-kinase inhibitors wortmannin and LY294002 inhibit autophagy in isolated rat hepatocytes".

(Continued)

*Primary Examiner* — Traviss C McIntosh, III
(74) *Attorney, Agent, or Firm* — Seed IP Law Group PLLC

(57) ABSTRACT

The present invention describes the identification and purification of 7-hydroxychromes that exhibit potent antioxidant activity. In one embodiment the present invention includes a method for providing an antioxidant to a host in need thereof, comprising administering an effective amount of a 7-hydroxychrome or a mixture of 7-hydroxychromones. The present invention includes methods that are effective in inhibiting free radical and oxidation caused damage through the simultaneous suppression of free radical generation and the suppression of the production of reactive oxygen species (ROS). The present invention also includes methods for preventing and treating ROS mediated diseases and conditions and diseases and conditions associated with other oxidative processes. The method for preventing and treating ROS mediated diseases and conditions and diseases and conditions associated with other oxidative processes is comprised of administering to a host in need thereof an effective amount of a composition comprised of a 7-hydroxychrome or a mixture of 7-hydroxychromones and a pharmaceutically acceptable carrier. Included in this invention is an improved method to isolate and purify 7-hydroxychromones from plant sources.

21 Claims, 8 Drawing Sheets

OTHER PUBLICATIONS

Budzianowski et al. (1991) Pol. J. Pharmacol. Pharm. 43:395-401, "Studies on Antioxidative Activity of Some C-Glycosylflavones".

Byeon et al. (1998) J. Investigative Dermatology 110:811-817, "Aloe Barbadensis Extracts Reduce the Production of Interleukin-10 After Exposure to Ultraviolet Radiation".

Cai (1996) J. Nat. Prod. 59:987-990, "Compounds from *Syzgium aromaticum* Possessing Growth Inhibitory Activity Against Oral Pathogens".

Conner et al. (1990) Phytochemistry 29:941, "Anthrone and Chromone Components of Aloe Cremnophila and A. Jackson II Leaf Exudates".

Constantino et al. (Jun. 3, 1999) J. Med. Chem. 42(11):1881-1893, "1-Benzopyran-4-one Antioxidants As Aldose Reductase Inhibitors".

Devi et al. (1999) Radiation Research 1(151):74-78, "In vivo Radioprotection by Ocimum Flavonoids: Survival of Mice".

Devi et al. (2000) Radiation Research 154(4):455-460, "Radiation Protection by the Ocimum Flavonoids Orientin and Vicenin: Mechanisms of Action".

Erickson et al. (1992) J. Med. Chem. 35:1526-1535, "(Aminoalkoxy)chromones. Selective Receptor Ligands".

Fernandes et al. (2002) Journal of Enzyme Inhibition and Medicinal Chemistry 17(1):45-48, "2-Styrylchromones As Novel Inhibitors Of Xanthine Oxidase. A Structure-Activity Study".

Fujimoto et al. (2002) Chem. Pharm. Bull. 50:330-336, "Five New Chromones Possessing Monoamine Oxidase Inhibitory Activity from an Ascomycete, Chaetonium quadrangulatum".

Fukyuasu et al. (1996) Chemical Abstracts Service, "Preventive Effects of Homonataloin and Aloesin on the UV-B Induced Immune Suppression. Investigation Using Contact Hypersensitivity Response".

Geiseg, (1999) New Zealand Science Monthly, pp. 6-8, "Reducing Free Radicals—A Dietary Revolution".

Ghannam,(1986) Hormone Res. 24:288-294, "The Antidiabetic Activity of Aloes: Preliminary Clinical and Experimental Observations".

Grindlay et al. (1986) J. of Ethnopharmacology 16:117-151, "The *Aloe vera* Phenomenon: A Review of the Properties and Modern Uses of the Leaf Parenchyma Gel".

Hart et al. (1988) J. Of Ethnopharmacology 23:61-71, "Two Functionally and Chemically Distinct Immunomodulatory Compounds in the Gel of *Aloe vera*".

Haynes et al. (1970) J. Chem. Soc. (C) 2581, "C-glycosyl Compounds".

Henry (1979) Cosmetics & Toiletries 94:42-50, "An Updated Review of *Aloe vera*".

Hirata et al. (1977) Z. Naturforsch 32c:731-734, "Biologically Active Constituents of Leaves and Roots of *Aloe arborescens* var. natalensis".

Holdsworth (1972) Dept. of Chem., Univ. of Papua and New Guinea, 322-325, "Chromones in Aloe Species".

Hutter et al. (1996) J. Nat. Prod. 59:541-543, "Antiinflammatory C-Glucosyl Chromone from *Aloe barbadensis*".

Inaba et al. (2000) Chem. Pharm. Bull. 48:131-139, "Synthesis and Antiinflammatory Activity of 7-Methanesulfonylamino-6-phenoxychromes. Antiarthritic Effect of the 3-Formylamino Compound (T-614) in Chromic Inflammatory Disease Models".

Jurenka et al. (1989) Comp. Biochem. Physiol. 93:253-255, "In Vitro Inhibition of Prostaglandin H Synthase by Compounds from the Exocrine Secretions of Lace Bugs".

Lee et al. (1997) Biochem. Mol. Biol. Int. 41:285-292, "Aloesin Up-Regulates Cyclin E/CDK2 Kinase Activity Via Inducing the Protein Levels of Cycline E, CDK2, and CDC25A in SK-HEP-1 Cells".

Lee et al. (2000) Free Radic Biol. Med. 28(2):261-265, "Isolation and Identification of a Phenolic Antioxidant from *Aloe barbadensis*".

Leoncini et al. (1991) Pharmacol. Res. 23:139-148, "Antiplatelet Effect of 2-(Diethylamino)-7-Hydroxychromone".

McCarthy et al. (1967) Heft 3:342, "The Distribution of Aloesin in some South African Aloe Species".

McKnight et al. (2002), International Aloe Science Council January:2, "Resource Data and Case Studies on *Aloe vera*".

Mebe (1987) Phytochemistry 26:2646, "2'-p-methoxycoumaroylaloeresin, a c-glucoside from aloe excels".

Occhiuto et al. (1991) Phytotherapy Research 5(1):9-14, "Comparative Antiarrhythmic And Anti-Ischaemic Activity Of Some Flavones In The Guinea-Pig and Rat".

Park et al. (1998) Phytochemical Analysis, 9:186-191, "Anaysis of 13 Phenolic Compounds in Aloe species by High Performance Liquid Chromatography".

Piao et al. (2002) Chem. Pharm. Bull. 50:309-31, "Mushroom Tyrosiinase Inhibition Activity of Some Chromones".

Pong et al. (1998) J. Neurochem. 71:1912-1919 "Inhibition of Phosphatidylinositol 3-Kinase Activity Blocks Cellular Differentiation Mediated by Glial Cell Line-Derived Neutrophic Factor in Dopaminergic Neurons".

Prabhakar et al. (1978) Journal of Molecular and Cellular Cardiology 10(1):80, "Cardiovascular Effects of Vitexin" (Abstract).

Rauwald et al. (1993) J. Of Chromatography 639:359-362, "High-performance liquid chromatographic separation and determination of diastereomeric anthrone-C-glucosyls in Cape aloes".

Rauwald et al. (1993) Z. Naturforsch 48c:1-4, "5-Hydroxyaloin A in the Genus Aloe Thin Layer Chromatographic Screening and High Performance Liquid Chromatographic Determination."

Simpson et al. (2003) Diabetes Research and Clinical Practice; 59:165-180, "The prevision of type 2 diabetes—lifestyle change or pharmacotheraphy? A challenge for the 21st century".

Tetko et al. (1995) Bioorg Khim. 21(10):809-815 "Evolutionary computation to reveal structure-activity relationships in 3-phenoxychrome and 3-phenoxy-4-hydroxycoumarin derivatives" (Abstract).

Witiak et al. (1975) J. Med. Chem. 18(9):934-942, "Synthesis of Ethyl 6-Substituted Chroman- and -Chromone-2-carboxylates. A Comparative Structure-Activity Study Employing the 6-Phenyl and Phenoxy Analogs in the Triton Hyperlipidemic Rat Model".

Yagi et al. (1987) Planta Medica 515-517, "Kanbara and Morinobu, Inhibition of Mushroom-Tyrosinase by Aloe Extract".

Yagi et al. (2002) Planta Medica 68(11):957-960, "Antioxidant, Free Radical Scavenging and Anti-Inflammatory Effects of Aloesin Derivatives in *Aloe vera*".

Office Action sent on Apr. 23, 2003 by U.S. Appl. No. 10/138,932.
Office Action sent on Nov. 18, 2003 by U.S. Appl. No. 10/138,932.
Office Action sent on Jun. 29, 2004 by U.S. Appl. No. 10/138,932.
Office Action sent on Jan. 8, 2008 by U.S. Appl. No. 11/085,896.
Office Action sent on Aug. 7, 2008 by U.S. Appl. No. 11/085,896.
International Search Report sent on Jul. 28, 2003 by ISA for PCT/US03/13935.

Beppu (2006) J Ethnopharmacol. 103(3):468-477, "Antidiabetic effects of dietary administration of *Aloe arborescens* Miller components on multiple low-dose streptozotocin-induced diabetes in mice: Investigation on hypoglycemic action and systemic absorption dynamics of aloe components".

Final Report on the Safety Assessment of *Aloe androgensis* Extract, . . . (2007), International Journal of Toxicology, 26(1):1-50.

Loots (2007) J Agric. Food Chem. 55(17):6891-6896, "*Aloe ferox* Leaf Gel Phytochemical Content, Antioxidant Capacity, and Possible Health Benefits".

Rajasekaran (2005) Biol. Trace Elem. Res. 108(1-3):185-195, "Mineral Contents of *Aloe vera* Leaf Gel and Their Role on Streptozotocin-Induced Diabetic Rats".

Rajasekaran (2005) Pharmacol. Rep. 57(1):90-96, "Antioxidant effect of *Aloe vera* gel extract in streptozotocin-induced diabetes in rats".

Strickland et al. (1998) Chemical Abstracts 128:974, reference No. 128: 235122s, Pelley, Kripke, "Cytoprotective Oligosaccharide from Aloe Preventing Damage to the Skin Immune System by UV Radiation".

Tanaka (2006) Biol. Pharm. Bull. 29(7):1418-142, Identification of Five Phytosterols from *Aloe vera* Gel as Anti-diabetic Compounds.

Third Party Observations filed Jan. 18, 2011 in EP application serial No. 03733934.8.

* cited by examiner

7-HYDROXY CHROMONES AS POTENT ANTIOXIDANTS

RELATED APPLICATION

This application is a continuation application of U.S application Ser. No. 11/085,896, filed Mar. 21, 2005, now U.S. Pat. No. 7,678,772, which is a divisional application of U.S application Ser. No. 10/138,932, filed May 3, 2002, now U.S. Pat. No. 6,884,783, both of which are entitled "7-Hydroxy Chromones As Potent Antioxidants," the contents of which are incorporated herein by reference in their entirety.

FIELD OF THE INVENTION

The present invention relates to the field of antioxidants. Specifically, this invention relates to the identification of a class of compounds, referred to herein as 7-hydroxychromones, which have potent antioxidant activity. More specifically, this invention relates to a method for the prevention and treatment diseases and conditions associated with reactive oxygen species (ROS) damage and other oxidation processes by administration of one or more 7-hydroxychromones. Included in this invention is an improved method to isolate and purify 7-hydroxychromones from plant sources.

BACKGROUND OF THE INVENTION

Reactive oxygen species (ROS) are produced by normal physiological processes in the body and play a significant role in the flow energy and information in all the living systems. (Voeikov (2001) Riv. Biol. 94:237-258). ROS also perform critical functions related to intercellular induction of apoptosis (Bauer (2000) Anticancer Res. 20:4115-4139), inflammation processes and immune responses. ROS are also generated as by-products of normal metabolic processes, from food additives, from environmental sources, such as ultraviolet radiation (Wenk et al. (2001) Curr. Probl. Dermatol. 29:83-94) and tobacco smoke (Stich et al. (1991) American Journal of Clinical Nutrition 53:298S-304S), and from many other pollutants. Reactive oxygen species (ROS) include oxygen related free radicals, such as superoxide ($O_2^{-\cdot}$), peroxyl ($ROO^{-\cdot}$), alkoxyl ($RO^{-\cdot}$), hydroxyl ($HO^{-\cdot}$), and nitric oxide ($NO^{-\cdot}$); and non-radical species, such as the singlet oxygen ($^1O_2$), hydrogen peroxide ($H_2O_2$) and hypochlorous acid (HOCl).

Cells have specific mechanisms to maintain homeostasis, which keep ROS levels in check. (Mates (2000) Toxicology 153:83-104). A number of different biological pathways are employed to maintain oxidative homeostasis within a cell. These pathways include the synthesis and recycling of γ-glutamyl-cysteinyl-glycine (Glutathion GSH) and the action of specific enzymes, such as SOD, catalases and peroxidases. (Deneke et al. (1989) Am. J. Physiol. 257: L163-L173). The generation and recycling of GSH is commonly known as the γ-glutamyl cycle. (Lieberman et al. (1995) Amer. J. Pathol. 147:1175-1185). This cycle, which is illustrated in FIG. 1, culminates in the production of the naturally occurring intracellular anti-oxidant, GSH. The maintenance of appropriate levels of GSH is very important to the redox state of the cell.

Superoxide anions are among the most reactive and damaging ROS produced by the mitochondria. Consequently, the regulation of their production and neutralization is a very important component of maintaining the cellular redox state. The enzyme superoxide dismutase (SOD) catalyzes the production of the less reactive hydrogen peroxide from superoxide anions, as illustrated by equation 1. The hydrogen peroxide produced is subsequently reduced to water by either catalase or glutathione peroxidase (GPx). (Wei et al. (2001) Chin. J. Physiol. 31:1-11).

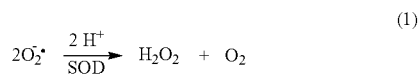

$$2O_2^{-\cdot} \xrightarrow{\text{2 H}^+ \atop \text{SOD}} H_2O_2 + O_2 \quad (1)$$

If the processes that maintain oxidative homeostasis in the cell get out of balance, free radical levels become dangerous, as these are highly reactive, molecules that damage DNA, proteins and components on cell membranes, eventually leading to cellular damage throughout the body and contributing a primary role in the aging process.

As a result of our modern diet and lifestyle, exposure to free radicals is increasing dramatically having a profound effect on our vulnerability to disease. The role of oxidative stress and its associated age related diseases is well established. Physiological changes that occur as we age, result in the loss of a homeostatic balance between the generation of ROS, which cause oxidative damage and the production of naturally occurring antioxidants, such as glutathione (GSH) and other regulatory enzymes (superoxide dismutase, catalase and peroxidases). As the origin of these ROS is the mitochondria, this loss of homeostasis that occurs during aging is known as the "mitochondrial theory of aging" (Simon (2000) Annals New York Acad. Sci. 908:219-225). Characteristic changes within the mitochondria during aging include, a decrease in the expression of the enzymes Cu/Zn-superoxide dismutase (SOD), which are responsible for "neutralizing" highly reactive and oxidative superoxide anions, accumulation of hydrogen peroxide and the reduction of mitochondrial glutathione pools. There is also a loss of intracellular and plasma GSH levels, resulting in an increasingly global oxidative environment within the human body during aging. This environment translates to a number of problems on both the cellular level and the level of the organism itself, as evidenced by the generation of chronic diseases of aging associated with oxidative damage.

For example, decreased GSH levels have been found in people suffering from debilitating neuro-degenerative diseases such as Alzheimer's Disease, Parkinson's disease, and amyotrophic lateral sclerosis (ALS). Cellular changes within individual cells include, physical damage to cellular components, as well as, alterations in cellular responses resulting from the increasingly oxidative environment. The physical damage includes, the oxidative damage to both cellular and mitochondrial DNA and the peroxidation of lipids within the cellular and mitochondrial membranes. These changes affect the integrity of both of these components and translate to impaired function. The oxidative environment also contributes to changes in many gene responses. (Forsberg et al. (2001) Arch. Biochem. Biophys. 389: 84-93). This is because transcription factors, such as NF-kB and AP-1 are controlled by changes in the redox state of cells. For example, NF-kB transcription factors are activated in oxidative environments. Thus, minute alterations in the redox state that occur during aging could dramatically change the way a cell responds to a particular stimulus. The altered responses can manifest themselves as increased apoptosis, cancers or the loss of function that ultimately cause many of the diseases related to aging. (Zs.-Nagy (2001) Annals New York Acad. Sci. 928:187-199).

ROS also a play critical role after brain injury, implicating them in the pathology of traumatic CNS damage and cerebral ischemia. (Lewen (2000), J. Neurotrauma 17:871-890). ROS caused oxidative stress in endothelial cells is a leading condition in the pathogenesis of many cardiovascular diseases (Touyz (2000) Curr. Hypertens. Rep. 2:98-105), pulmonary diseases (Berry et al. (2001) Curr. Opin. Nephrol. Hypertens. 10:247-255) and metabolic disorders (Takahashi (2000) Nippon Rinsho 58:1592-1597).

Protection of alveolar epithelial cells and vascular endothelia cells against pulmonary (Muzykantov (2001) Antioxid. Redox Signal 3: 39-62) and vascular endothelium oxidative stress (Muzykantov (2001) J. Control Release 12:1-21) has been investigated via delivery antioxidative enzymes, such as SOD and catalase. The beneficial effects from dietary antioxidants, such as resveratrols (Hung et al. (2002) Br. J. Pharmacol. 135:1627-1633) and alpha-lipoic acid (Takaoka et al. (2002) Clin. Exp. Pharmacol. 29:189-194) in reducing the incidence of coronary heart diseases, butylated hydroxytoluene and β-carotene in photocarcinogenesis (Black (2002) Front Biosci. 7:D1044-1055) has been documented. Even though antioxidants may reduce free radicals generated by radiotherapy and chemotherapy, there is no evidence suggesting that they interfere with conventional cancer therapy. Clinical evidence indicates that cancer patients given antioxidants exhibit higher tolerance and decreased side effects, resulting from treatment and further that they live longer and have a higher quality of life. (Lamson et al. (1999) Altern. Med. Rev. 4:304-329). While these diseases represent extreme examples, it is well documented that the skewing of the redox state toward an oxidative environment is a characteristic of the aging process. Therefore, the average person benefits by maintaining a homeostatic oxidative balance. Because the oxidative damage that occurs during the aging process can be directly linked to pathological aspects of these diseases, controlling or restoring the homeostatic balance of the oxidative state is of great interest to the medical industry as a whole. Consequently, anti-oxidants have a secure place within the Dietary Supplemental Health and Education Act (DSHEA) arena, as evidenced by the number of antioxidant products targeted for the anti-aging market.

Antioxidant defense mechanisms are species specific and heavily influenced by nutrition, since important antioxidants, such as, ascorbic acid and α-tocopherol cannot be synthesized by humans and therefore, must be obtained from ones diet. (Benzie (2000) Eur. J. Nutr. 39:53-61). Antioxidants are very popular dietary supplements in the nutritional and cosmeceutical industries. Types of products promoted as antioxidants include, vitamins (i.e., Vc, Ve, Vb, β-carotene), minerals (i.e., selenium), amino acids (i.e., lysine, cysteine, n-acetyl cysteine, lipoic acid), phenolic acids (i.e., curcumin, rosveratrol, chetechins, EGCG), flavanoids (i.e., rutin, quercetine, etc.) (Pietta (2000) J. Nat. Prod. 63:1035-1042), anthrocynadines, pycnogenol, coumarine derivatives, polyphenols (i.e., tannins) and many different types of botanical extracts. Antioxidant products include polyunsaturated fatty acids (PUFAs) and specialty amino acids, claims for which range from reducing the risk of heart disease to treating joint problems and easing depression. β-carotene is a major antioxidant, which has been shown to reduce the risk of prostate cancer. β-carotene is primarily available in dietary supplements, specifically multivitamin formulations and single-entity soft gel capsules. The product is a popular antioxidant, thought to help prevent many diseases.

Lycopene, an up-and-coming phytochemical in the β-carotene family, is receiving increased attention because of its promise as an antioxidant. The new product, Lycopene 5% TG, is readily available in multivitamin, antioxidant, straight and chewable formulations. Sabinsa Corp. has developed a new, colorless tumeric root extract, tetrahydrocurcuminoids (THC), for use in dietary supplements and cosmeceuticals as a bioprotectant and multipurpose antioxidant that does not stain. THC is a free radical scavenger, preventing free radical chain reactions by neutralizing existing free radicals and/or maintaining a reducing environment around the cells and preventing the formation of free radicals; and acting as a chelating agent to generate non-active complexes with prooxidatant metals. It is claimed that some antioxidants enhance the protective capability of the cell wall, thereby bolstering the cell's defense against free radicals and repairing damage done to cells by free radicals. However, there is not much scientifically sound data to prove the efficacy of these antioxidants.

The Oxygen Radical Absorption Capacity (ORAC) assay is a method for measuring total serum antioxidant activity. (Cao et al. (1993) Free Rad. Biol. Med. 14:303-311). It can be used to quantitatively measure the total antioxidant capacity, as well as, qualitatively measure the levels of fast versus slow acting antioxidants in a blood serum sample. The assay utilizes the free radical sensitive fluorescent indicator protein β-phycoerythrin (β-PE) to monitor the effectiveness of various serum antioxidants in protecting β-PE from becoming damaged by free radicals. Assay results are quantitated by allowing the reaction to reach completion and then integrating the area under the kinetic curve relative to a blank reaction containing no antioxidant. The area under the curve is proportional to the concentration of all the antioxidants present in the sample. (DeLang and Glazer (1989) Analyt. Biochem. 177:300-306).

The Lipid Peroxidation Inhibition Capacity (LPIC) assay is a method for measuring the ability of a sample to inhibit the initiation and propagation of a spontaneous lipid peroxidation reaction. Lipid peroxidation represents the major mechanism of lipid destruction occurring in an organism. This reaction is also an important source of reactive oxygen species. In part, lipid peroxidation is controlled in vivo by:

1) the chelation of trace metals, such as iron and copper, that are involved in the initiation of lipid peroxidation reactions; and 2) the presence of antioxidants that terminate the propagation reaction once it is initiated.

Lipid peroxidation is believed to be one of the major destructive reactions, occurring in the plasma components and blood vessel walls, leading the onset of cardiovascular disease. (Riemersma et al. (1991) Lancet 337:1-5). Thus, a principal role of antioxidants and metal-chelating components in the serum is the protection of the entire cardiovascular system through the control of lipid peroxidation. (Stampfer et al. (1993) New England Journal of Medicine 328:1444-1449; Rimm et al. (1993) New England Journal of Medicine 328:1450-1456.). Metal chelators, such as ferritin for iron and metallothionein for copper are well known, but other serum constituents, such as urate, which can chelate iron, may also be important. (Maples et al. (1988) J. Biol. Med. 263:1709-1712). Antioxidants, such as α-tocopherol, are known to prevent propagation of lipid peroxidation reactions, but there may be many other serum constituents that could be equally or even more important than α-tocopherol. (Stahelin et al. (1984) Journal of the National Cancer Institute 73:1463-1468). The LPIC assay measures how well a sample is able to both inhibit and terminate a lipid peroxidation reaction. The LPIC value complements the ORAC value. The ORAC assay provides information on total antioxidant capacity, whereas the LPIC assay provides information on both total antioxidant capacity and on the status of metal catalysts in effectively protecting against in vivo lipid peroxidation reactions.

Chromones are a specific type of aromatic compounds having a benzopyran-4-one as their major skeletal structure as illustrated by the following general structure:

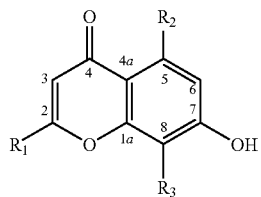

wherein $R_1$, $R_2$ and $R_3$ are independently selected from the group consisting of —H, —OH, —$CH_3$, —SH, alkyl, alkenyl, oxoalkyl, oxoalkenyl, hydroxylalkyl, hydroxylalkenyl, —$OCH_3$, —$SCH_3$, —OR, —SR, —$NH_2$, —NRH, —$NR_2$, —$NR_3^+X^-$, esters of the mentioned substitution groups, including, but not limited to, gallate, acetate, cinnamoyl and hydroxyl-cinnamoyl esters, trihydroxybenzoyl esters and caffeoyl esters; thereof carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized chromones;

wherein said alkyl and/or alkenyl group is a straight and/or branched chain having between 1-20 carbon atoms with and/or without double bonds in different positions;

X is selected from the group of pharmaceutically acceptable counter anions including, but not limited to hydroxyl, chloride, iodide, sulfate, phosphate, acetate, fluoride, carbonate, etc.; and R is an alkyl group having between 1-20 carbon atoms. To date there are only 183 chromones isolated from natural sources. (The Combined Chemical Dictionary, Chapman & Hall/CRC, Version 5:1 June 2001).

Chromones reportedly exhibit monoamine oxidase inhibitory activity (Fujimoto et al. (2002) Chem. Pharm. Bull. 50:330-336), tyrosinase inhibitory activity (Piao et al. (2002) Chem. Pharm. Bull. 50:309-311), anti-platelet effects (Leoncini et al. (1991) Pharmacol. Res. 23:139-148), inhibitory activity of phosphatidylinositol-3-kinase (Pong et al. (1998) J. Neurochem. 71:1912-1919; Blommaart et al. (1997) Eur. J. Biochem 243:240-246), growth inhibitory activity against oral pathogens (Cai (1996) J. Nat. Prod. 59:987-990), prostaglandin H synthase inhibitory activity (Jurenka et al. (1989) Comp. Biochem. 93:253-255). Chromones also possess therapeutic efficacy against type II collagen-induced arthritis in rats (Inaba et al. (2000) Chem. Pharm. Bull. 48:131-139) and hypolipidemic activity (Witiak et al. (1975) J. Med. Chem. 18:934-942; Tetko et al. (1995) Bioorg Khim. 21:809-815). It has also been reported that chromones can function as selective sigma receptor ligands (Erickson et al. (1992) J. Med. Chem. 35:1526-1535). Based on animal studies, chromones are easily absorbed and metabolized (Crew et al. (1976) Xenobiotica 6:89-100) and the c-glucosyl bond of aloesin can be cleaved by human intestinal bacteria. (Che et al. (1991) Chem. Pharm. Bull. 39:704-708).

*Aloe* is an intricate plant that contains many biologically active substances. (Cohen et al. in *Wound Healing/Biochemical and Clinical Aspects*, 1st ed. WB Saunders, Philadelphia (1992)). Over 300 species of *Aloe* are known, most of which are indigenous to Africa. Studies have shown that the biologically active substances are located in three separate sections of the aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, *Aloe* products have been used in dermatological applications for the treatment of burns, sores and other wounds. These uses have stimulated a great deal of research in identifying compounds from *Aloe* plants that have clinical activity, especially anti-inflammatory activity. (See, e.g., Grindlay and Reynolds (1986) J. of Ethnopharmacology 16:117-151; Hart et al. (1988) J. of Ethnopharmacology 23:61-71). As a result of these studies there have been numerous reports of *Aloe* compounds having diverse biological activities, including anti-tumor activity, anti-gastric ulcer, anti-diabetic, anti-tyrosinase activity (see, e.g., Hirata and Suga et al. (1977) Z. Naturforsch 32c:731-734) and antioxidant activity (Yu and Lee, U.S. Pat. No. 5,939, 395).

Chromones isolated from various *Aloe* species have been reported to have diverse biological activity. Aloesin (FIG. 2) reportedly inhibits tyrosinase activity (Jones et al. Journal of Pigment Cell Research, Acceptance, Feb. 10, 2002) and up-regulates cyclin E-dependent kinase activity (Lee et al. (1997) Biochem. Mol. Biol. Int. 41:285-292). A c-glycosyl chromone isolated from *Aloe barbadensis* demonstrates anti-inflammatory activity (Hutter et al. (1996) J. Nat. Prod. 59:541-543) and antioxidant activity similar to that of alpha-tocopherol based on a rat brain homogenates model (Lee et al. Free Radic Biol. Med. 28:261-265).

*Aloe barbadensis* leaves and its bitter principles exhibit effects on blood glucose level in normal and alloxan diabetic mice (Ajabnoor (1990) J. Ethnopharmacol. 28:215-220) and dried sap of various *Aloe* species demonstrates anti-diabetic activity in clinical studies (Ghannam, (1986) Horm Res. 24:288-294).

Yagi et al. disclose a group of compounds isolated from *Aloe*, particularly aloesin and one of its derivatives, 2"-O-feruloylaloesin, which are effective inhibitors of tyrosinase. (Yagi et al. (1987) Plant Medica 515-517). Biochemical testing of the enzyme inhibition by means of the Lineweaver Burk diagram showed that 2"-feruloylaloesin was a noncompetitive inhibitor of tyrosinase, while aloesin is a competitive inhibitor. Aloesin is a C-glucosylated 5-methyl-chromone (Holdsworth (1972) *Chromones in Aloe Species, Part I-Aloesin PM* 19(4):322-325). In vitro, aloesin is a strong inhibitor of tyrosinase activity (Yagi et al. (1987) Planta Medica 515-517). In assays of tyrosinase activity on the substrate L-DOPA, aloesin is capable of 50% inhibition at a concentration of 0.2 mM.

U.S. Pat. No. 6,083,976, entitled "Method of Synthesis of Derivatives of Aloesin," describes a novel method for the synthesis of derivatives of aloesin alkylated at the C-7 hydroxyl group. The alkylated aloesins, produced by this method have the functionality of aloesin, a tyrosinase-inhibiting compound with skin whitening activity, but have greater biological activity than aloesin as indicated by in vitro tyrosinase assays. Additionally, the alkyl group makes the derivatized aloesins more fat soluble than aloesin, allowing them to be retained in the stratum corneum of the skin more effectively than aloesin. As a result, the alkylated aloesins are more potent and faster acting skin lightening agents than aloesin.

U.S. Pat. No. 6,123,959, entitled "Aqueous Composition Comprising Active Ingredients for the De-Pigmentation of the Skin," describes aqueous compositions comprising liposomes of phospholipids, and at least one competitive inhibitor of an enzyme for the synthesis of melanin, in combination with at least one non-competitive inhibitor of an enzyme for the synthesis of melanin. The competitive inhibitors of the invention include aloesin and derivatives thereof. The invention also includes the use of the compositions for the depigmentation of skin. Each of these patents is incorporated herein by reference in their entirety.

To date, known methods for purifying aloesin, as well as, other chromones involve the use of chromatography. (See e.g., Rauwald and Beil (1993) J. of Chromatography 639: 359-362; Rauwald and Beil (1993) Z. Naturforsch 48c:1-4; Conner et al. (1990) Phytochemistry 29:941; Holdsworth (1972) *Chromones in Aloe Species, Part I-Aloesin* PM 19(4): 322-325; Mebe (1987) Phytochemistry 26:2646; Haynes et al. (1970) J. Chem. Soc. (C) 2581; McCarthy and Haynes (1967) *The Distribution of Aloesin in Some South African Aloe Species;* Heft 3 342). These procedures were developed for chemical analysis and are not practical for preparative scale production of aloesin. In U.S. patent application Ser. No. 09/792,104, filed Feb. 26, 2001, entitled "Method of Purification of Aloesin," which is incorporated herein by reference in its entirety, a method for purification of aloesin using crystallization is disclosed. Applicant knows of no report or suggestion of a method for the purification of chromones from *Aloe* and other indicated species using with polyamide or LH-20 column chromatography.

SUMMARY OF THE INVENTION

The present invention describes the identification and purification of 7-hydroxychromes that exhibit potent antioxidant activity. In one embodiment the present invention includes a method for providing an antioxidant to a host in need thereof, comprising administering an effective amount of a 7-hydroxychrome or a mixture of 7-hydroxychromones.

The present invention also includes methods that are effective in inhibiting lipid peroxidation through the simultaneous suppression of free radical generation and suppression of the production of reactive oxygen species (ROS). The method for inhibiting lipid peroxidation is comprised of administering a composition comprising a 7-hydroxychrome or a mixture of 7-hydroxychromones to a host in need thereof.

The present invention also includes methods for preventing and treating ROS mediated diseases and conditions and diseases and conditions associated with other oxidative processes. The method for preventing and treating ROS mediated diseases and conditions and diseases and conditions associated with other oxidative processes is comprised of administering to a host in need thereof an effective amount of a composition comprised of a 7-hydroxychrome or a mixture of 7-hydroxychromones and a pharmaceutically acceptable carrier.

The 7-hydroxychromones that can be used in accordance with the following include compounds illustrated by the following general structure:

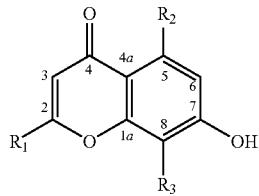

wherein
$R_1$, $R_2$ and $R_3$ are independently selected from the group consisting of —H, —OH, —CH$_3$, —SH, alkyl, alkenyl, oxoalkyl, oxoalkenyl, hydroxylalkyl, hydroxylalkenyl, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters; thereof carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized chromones;

wherein said alkyl and/or alkenyl group is a straight and/or branched chain having between 1-20 carbon atoms with and/or without double bonds in different positions;

X is selected from the group of pharmaceutically acceptable counter anions including, but not limited to hydroxyl, chloride, iodide, sulfate, phosphate, acetate, fluoride, carbonate, etc.; and R is an alkyl group having between 1-20 carbon atoms. In a preferred embodiment of this invention the 7-hydroxychromone is selected from aloesin (FIG. 2) or aloeresin A (FIG. 3).

The 7-hydroxychromones of this invention may be obtained by synthetic methods or may be isolated from the genera of numerous plant families, including but not limited to *Acacia, Adina, Aloe, Alternaria, Amoora, Antidesma, Artemisia, Baeckia, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces* and *Zonaria*. In a preferred embodiment, the plant is selected from the group, including but not limited to, *Acacia catechu, Acacia concinna, Aloe arborescens, Aloe barbadensis, Aloe cremnophila, Aloe ferox, Aloe saponaria, Aloe vera, Aloe vera* var. *chinensis, Antidesma membranaceum, Artemisia capillaries, Baeckia frutescens, Epimedium sagittatum, Garcinia dulcis, Hypericum japonicum, Polygonum cuspidatum, Sophora tomentosa* and *Stephanitis rhododendri*.

The 7-hydroxychromones can be found in different parts of plants, including but not limited to stems, stem barks, trunks, trunk barks, twigs, tubers, roots, root barks, young shoots, seeds, rhizomes, flowers and other reproductive organs, leaves and other aerial parts.

The method of this invention can be used to treat and prevent a number of ROS mediated diseases and conditions including, but not limited to, atherosclerosis, coronary heart diseases, cataracts, dementia, Alzheimer's disease, cognitive dysfunction, diabetes mellitus, cancer, skin photo aging, skin wrinkles, sun burns, melanoma, and other degenerative processes associated with aging.

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of the individual and/or a mixture of multiple 7-hydroxy chromones isolated from a single source or multiple sources that include, but not limited to, synthetically obtained, naturally occurring, or any combination thereof.

The present invention also includes an improved method for the isolation and purification of chromones, particularly 7-hydroxychromones, from plants containing these compounds. The method of the present invention comprises: a) extracting the ground biomass of a plant containing a chromone, particularly a 7-hydroxychromone; b) neutralizing and concentrating said extract; and c) purifying said neutralized and concentrated extract using a chromatographic method, including but not limited to polyamide, LH-20 or reverse phase chromatography. In a preferred embodiment of the invention the extract is purified using a method selected from the group consisting of recrystallization, precipitation, solvent partition and/or chromatographic separation. The present invention provides a commercially viable process for the isolation and purification of chromones having desirable physiological activity.

It is to be understood that both the foregoing general description and the following detailed description are exemplary and explanatory only and are not restrictive of the invention as claimed.

DETAILED DESCRIPTION OF THE INVENTION

Various terms are used herein to refer to aspects of the present invention. To aid in the clarification of the description of the components of this invention, the following definitions are provided.

Figure 1:
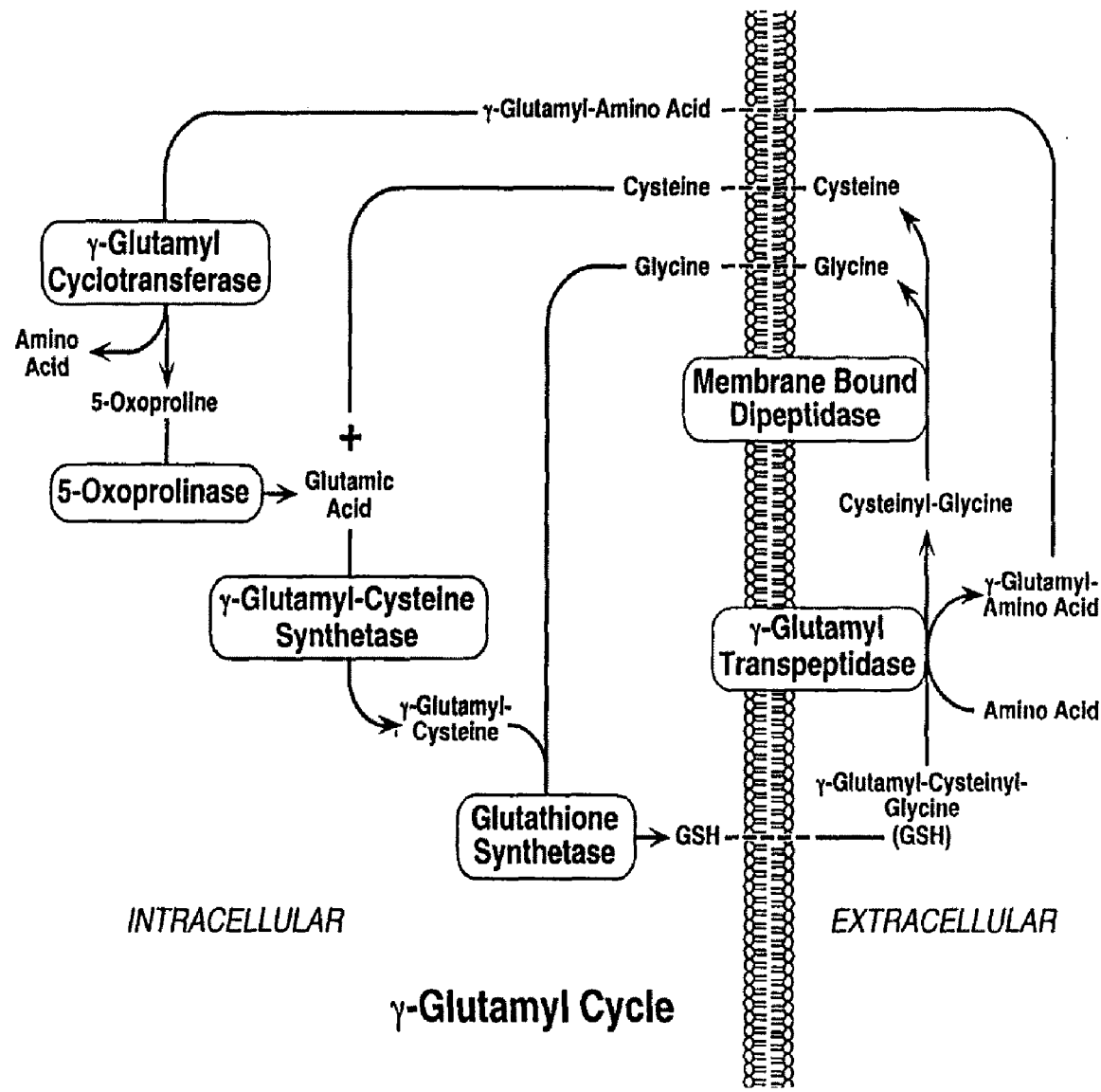
FIG. 1 depicts schematically a γ-Glutamyl Cycle.
Figure 2:
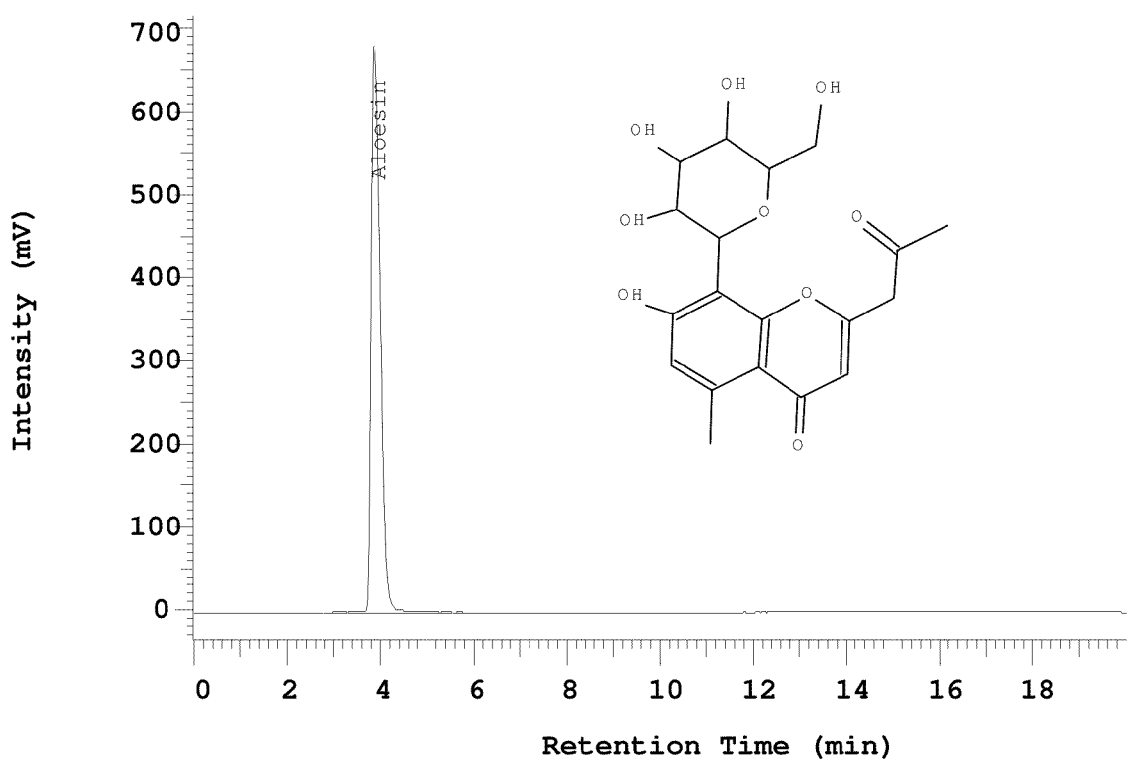
FIG. 2. depicts the high-pressure liquid chromatography (HPLC) chromatogram of Aloesin.

"Chromones" are a specific class of natural products having a benzopyran-4-one as the major structural skeleton as illustrated by the following general structure:

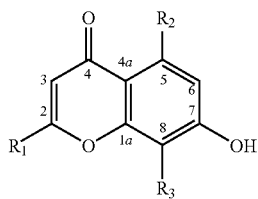

wherein $R_1$, $R_2$ and $R_3$ are independently selected from the group consisting of —H, —OH, —CH$_3$, —SH, alkyl, alkenyl, oxoalkyl, oxoalkenyl, hydroxylalkyl, hydroxylalkenyl, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters; thereof carbon, oxygen, nitrogen or sulfur glycoside of a single or a combination of multiple sugars including, but not limited to, aldopentoses, methyl aldopentose, aldohexoses, ketohexose and their chemical derivatives thereof; dimer, trimer and other polymerized chromones;

wherein said alkyl and/or alkenyl group is a straight and/or branched chain having between 1-20 carbon atoms with and/or without double bonds in different positions;

X is selected from the group of pharmaceutically acceptable counter anions including, but not limited to hydroxyl, chloride, iodide, sulfate, phosphate, acetate, fluoride, carbonate, etc.; and R is an alkyl group having between 1-20 carbon atoms. In a preferred embodiment of this invention the 7-hydroxychromone is selected from aloesin (FIG. 1) or aloeresin A (FIG. 2).

The term "Aloe" refers to the genus of South African plants of the Liliaceae family of which the Aloe ferox is one of the species. Aloe chromones are present primarily in the whole leaf of a number of different species of Aloe.

The term "Aloe extract" is defined as the dried juice of the whole leaf of various species of the Aloe plant. The "Aloe extract" used in the examples of this invention was prepared by "whole-leaf processing" of the whole leaf of various Aloe species. In one example, whole leaves obtained from the Aloe barbadensis plant were ground, filtered, treated with cellulase (optional) and activated carbon and lyophilized. The lyophilized powder was reconstituted with the chromatography solvent prior to use. In another example, the exudate from aloe leaves was suspended in water, followed by contact with an appropriate chromatography solvent prior to use.

"Therapeutic" as used herein, includes treatment and/or prophylaxis. When used, therapeutic refers to humans, as well as, other animals.

"Pharmaceutically or therapeutically effective dose or amount" refers to a dosage level sufficient to induce a desired biological result. That result may be the delivery of a pharmaceutical agent, alleviation of the signs, symptoms or causes of a disease or any other desirous alteration of a biological system.

A "host" is a living subject, human or animal, into which the compositions described herein are administered.

Note, that throughout this application various citations are provided. Each citation is specifically incorporated herein in its entirety by reference.

The present invention describes the identification and purification of 7-hydroxychromes that exhibit potent antioxidant activity. In one embodiment the present invention includes a method for providing an antioxidant to a host in need thereof, comprising administering an effective amount of a 7-hydroxychrome or a mixture of 7-hydroxychromones.

The present invention also includes methods that are effective in inhibiting lipid peroxidation through the simultaneous suppression of free radical generation and suppression of the production of reactive oxygen species (ROS). The method for inhibiting lipid peroxidation is comprised of administering a composition comprising a 7-hydroxychrome or a mixture of 7-hydroxychromones to a host in need thereof.

The present invention also includes methods for preventing and treating ROS mediated diseases and conditions and diseases and conditions associated with other oxidative processes. The method for preventing and treating ROS mediated diseases and conditions and diseases and conditions associated with other oxidative processes is comprised of administering to a host in need thereof an effective amount of a composition comprised of a 7-hydroxychrome or a mixture of 7-hydroxychromones and a pharmaceutically acceptable carrier.

The 7-hydroxychromones that can be used in accordance with this invention include compounds illustrated by the general structure set forth above. In a preferred embodiment of this invention the 7-hydroxychromone is selected from aloesin (FIG. 1) or aloeresin A (FIG. 2). The 7-hydroxychromones of this invention may be obtained by synthetic methods or may be isolated from the genera of numerous plant families, including but not limited to *Acacia, Adina, Aloe, Alternaria, Amoora, Antidesma, Artemisia, Baeckia, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces* and *Zonaria*. In a preferred embodiment, the plant is selected from the group, including but not limited to, *Acacia catechu, Acacia concinna, Aloe arborescens, Aloe barbadensis, Aloe cremnophila, Aloe ferox, Aloe saponaria, Aloe vera, Aloe vera* var. *chinensis, Antidesma membranaceum, Artemisia capillaries, Baeckia frutescens, Epimedium sagittatum, Garcinia dulcis, Hypericum japonicum, Polygonum cuspidatum, Sophora tomentosa* and *Stephanitis rhododendri*.

The 7-hydroxychromones can be found in different parts of plants, including but not limited to stems, stem barks, trunks, trunk barks, twigs, tubers, roots, root barks, young shoots, seeds, rhizomes, flowers and other reproductive organs, leaves and other aerial parts.

Examples 1, 2 and 3 describe the isolation and purification of two representative 7-hydroxychromones, aloesin and aloeresin A. Aloesin and aloeresin A were isolated from the exudates of the leaves of *Aloe ferox* in a purity of 95.2% and 61.5%, respectively.

As provided in Example 1, aloesin was isolated and purified using the methods described in U.S. patent application Ser. No. 09/792,104, filed Feb. 26, 2001, entitled "Method of Purification of Aloesin," which is incorporated herein by reference in its entirety. Aloesin can be obtained from *Aloe* exudates, such as aloe bitters or from other sources, including but not limited to, *Aloe* leaves, rinds, and whole plants containing this compound as a component.

The isolation and purification of aloesin A is described in Examples 2 and 3. In a typical separation, plant material containing aloeresin A (typically aloe bitters) is extracted in 10-100% alcohol (or other organic miscible solvent) in water (typically 30% methanol in water). The aloesin A is then purified using typical chromatographic media, particularly polyamide or LH-20, and/or reversed phase media. The extract solution is concentrated and/or directly applied to a bed of polyamide resin and/or a reversed phase based material. The column bed is then washed with 0-30% methanol (or other water soluble organic solvent; typically 2 column volume of 30% methanol in water) until all other compounds (typically aloesin and anthraquinones) are eluted. The column bed is then eluted with 30-100% organic solvent in water (typically two column volumes of 100% acetone). This fraction is then concentrated to obtain aloeresin A.

Figure 3:
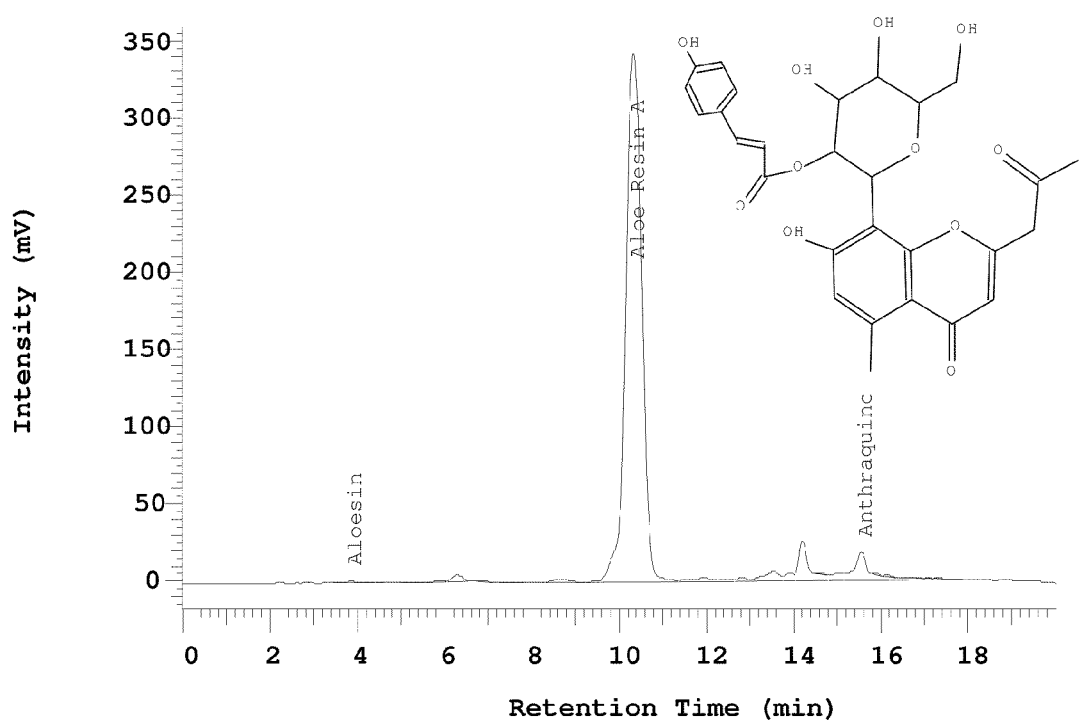
FIG. 3. depicts the HPLC chromatogram of Aloeresin A.
Figure 4:
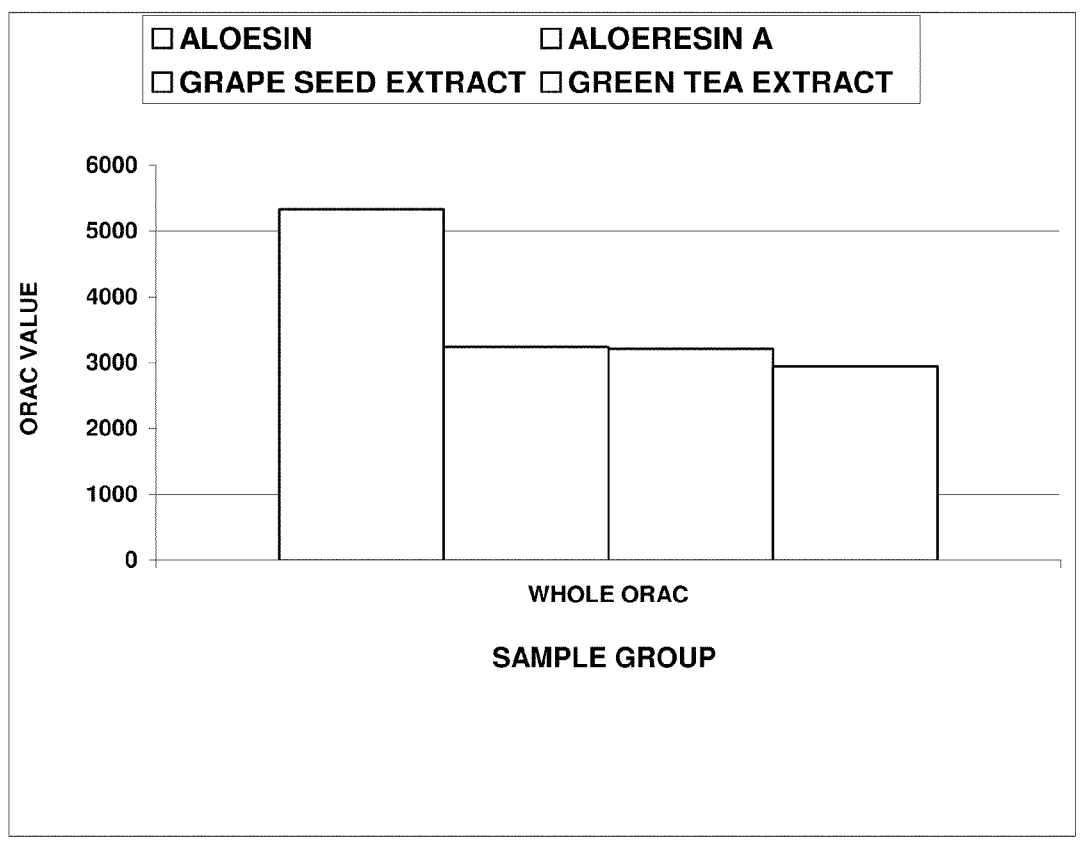
FIG. 4 illustrates graphically the whole ORAC value of aloe chromones Aloesin and Aloeresin A relative to grape seed extract and green tea extract.
Figure 5:
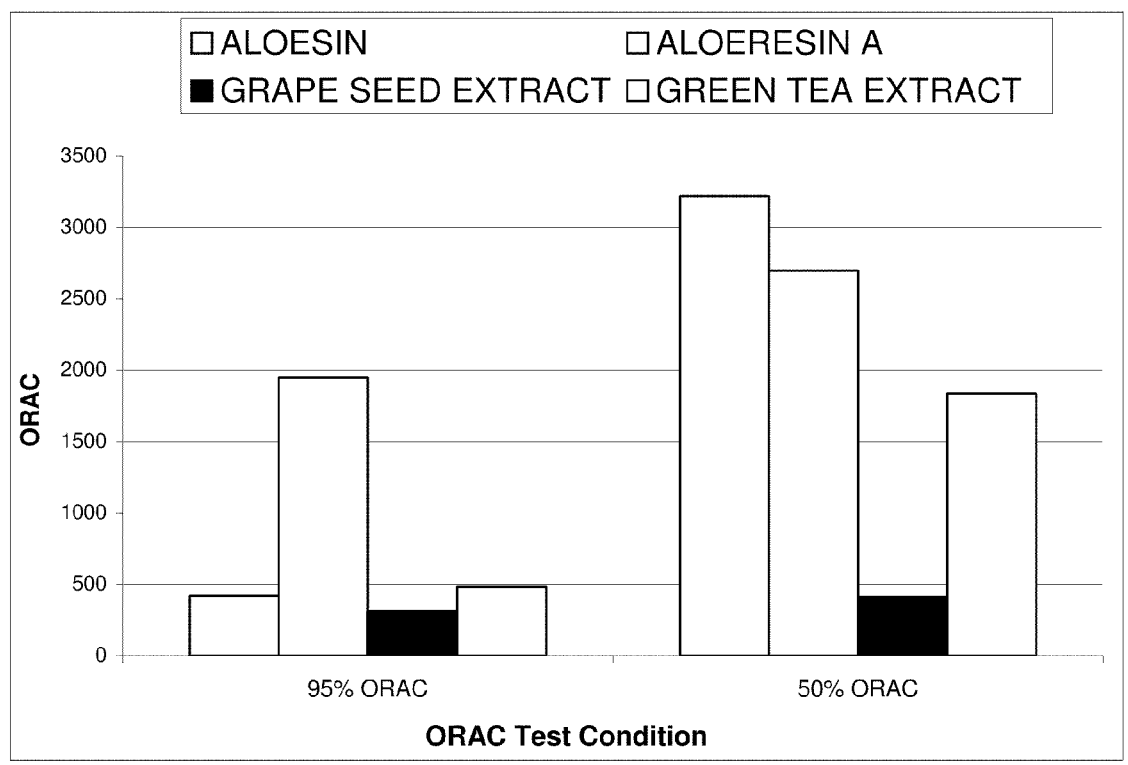
FIG. 5 illustrates graphically the fast and slow anti-oxidant activities of aloe chromones Aloesin and Aloeresin A relative to grape seed extract and green tea extract.

Example 4 describes the measurement of the Oxygen Radical Absorbance Capacity (ORAC) for both aloesin and aloeresin A, relative to grape seed extract and green tea extract. The results are set forth in FIG. 4. With reference to FIG. 4, it can be seen that aloesin had much higher whole ORAC value than aloeresin A and the standardized green tea and grape seed extracts. Aloeresin A had a whole ORAC value of 33 and 299 higher than green tea and grape seed extracts, respectively. Example 5 describes the measurement of fast and slow ORAC for the four compositions tested in Example 4. The results of this assay are set forth in FIG. 5. Aloeresin A was four times more potent as a fast antioxidant, than the other three compositions tested. Aloesin, however, was more potent as a slow acting antioxidant. Aloesin was over 70% more active than green tea extract and more than six times more active than grape seed extract at 50% ORAC conditions. Aloeresin A was also a superior antioxidant relative to grape seed and green tea extracts under these conditions. Both aloesin and aloesin A contain phenolic hydroxyl group in the C-7 position (see FIGS. 2 and 3). This hydroxyl group is very easily oxidized by reactive oxygen species (ROS) to form a ketone group. The extra hydroxyl cinnamoyl group in aloeresin A does not enhance the whole ORAC value of this compound. However, it significantly changes its polarity, which may be the reason that this compound is a superior fast antioxidant.

Example 6 describes the evaluation of Lipid Peroxidation Inhibition Capacity (LPIC) for aloeresin A, relative to vitamin C and α-tocopherol. As noted above, lipid peroxidation is believed to be a major destructive reaction, occurring in the plasma components and blood vessel walls and contributing to cardiovascular disease. The experiment described in the Example 6, was designed as an indicator of free radical induced lipid destruction occurring in an organism. The LPIC assay measures the ability of a sample to both inhibit and terminate a lipid peroxidation reaction. The LPIC value complements the ORAC value. The ORAC assay provides information on total antioxidant capacity, whereas the LPIC assay provides information on both total antioxidants and the status of metal catalysts in effectively protecting against in vivo lipid peroxidation reactions.

Figure 6:
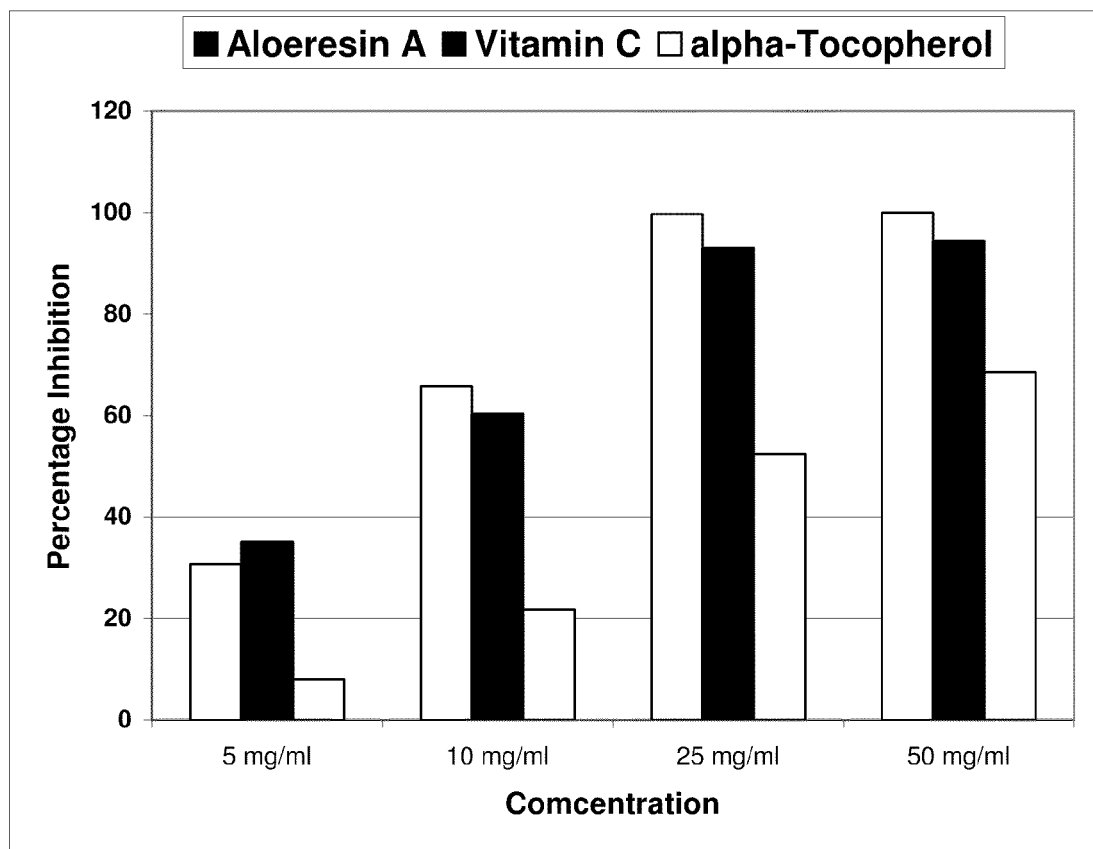
FIG. 6 illustrates graphically the lipid peroxidation inhibition capacity (LPIC) of Aloeresin A relative to vitamin C and alpha-tocopherol.

The results of the assay described in Example 6 are set forth in FIG. 6. As illustrated in the FIG. 6, aloeresin A is a stronger antioxidant than either α-tocopherol or vitamin C, as measured by lipid peroxidation inhibition capacity (LPIC) from concentrations of 10 mg/mL to 50 mg/mL. It also inhibited lipid peroxidation 30.7% even at a concentration as low as 5 mg/mL vs. below 10% for α-tocopherol.

Lipid peroxidation is controlled in vivo by chelation of trace metals, such as, iron and copper that are involved in the initiation of lipid peroxidation reactions; and by the presence of antioxidants that terminate the propagation reaction once it is initiated. Metal chelators, such as ferritin for iron and metallothionein for copper, are well known, but other serum constituents, such as urate, which can chelate iron, may also be important. Antioxidants, such as alpha-tocopherol, are known to prevent propagation of lipid peroxidation reactions, but there may be many other serum constituents that could be equally or more important. Since aloeresin A contains a ketone, as well as, a number of hydroxyl groups on the benzopyran-4-one ring and on the sugar unit, it is functional as both a metal chelator and a free radical scavenger. Thus, a principal role of chromone antioxidants is the protection of the entire cell system through the control of lipid peroxidation by both chelation and the scavenging of free radicals.

Figure 7:
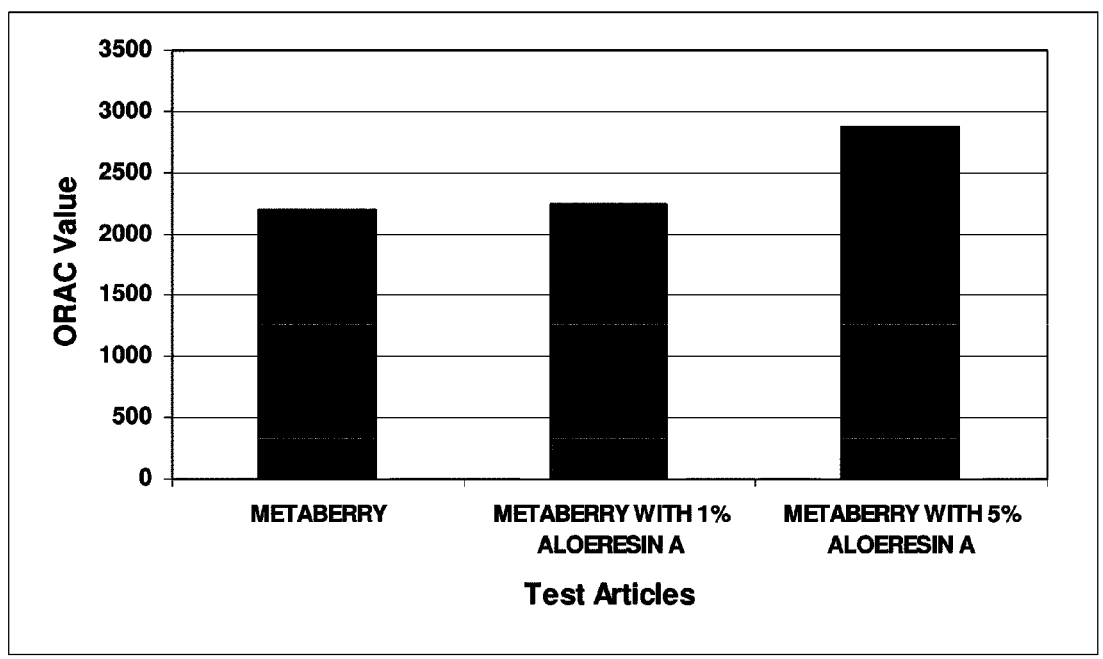
FIG. 7 depicts graphically the improvement of ORAC value of a metaberry drink upon the addition of 1% and 5% Aloeresin A.

7-hydroxychromones not only possess high ORAC and LPIC values in and of themselves, they can also improve the antioxidative capacity of a product if they are appropriately formulated into the product as illustrated in Examples 7 and 8. In the example 6, it is demonstrated that aloeresin A, at a concentration of 5%, increases the ORAC value of a multiple berry fruit drink by 31.3%. The results of Example 7 are set forth in FIG. 7. In Example 8, it is demonstrated that aloeresin A increases LIPC of a formulated antioxidant product by 19% to 38% at a dosage of 50 mg to 250 mg/serving.

The method of this invention can be used to treat and prevent a number of ROS mediated diseases and conditions including, but not limited to, atherosclerosis, coronary heart diseases, cataracts, dementia, Alzheimer's disease, cognitive dysfunction, diabetes mellitus, cancer, skin photo aging, skin wrinkles, sun burns, melanoma, and other degenerative processes associated with aging.

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of the individual and/or a mixture of multiple 7-hydroxy chromones isolated from a single source or multiple sources that include, but not limited to, synthetically obtained, naturally occurring, or any combination thereof.

The present invention also includes an improved method for the isolation and purification of chromones, particularly 7-hydroxychromones, from plants containing these compounds. The method of the present invention comprises: a) extracting the ground biomass of a plant containing a chromone, particularly a 7-hydroxychromone; b) neutralizing and concentrating said extract; and c) purifying said neutralized and concentrated extract using a chromatographic method, including but not limited to polyamide, LH-20 or reverse phase chromatography. In a preferred embodiment of the invention the extract is purified using a method selected from the group consisting of recrystallization, precipitation, solvent partition and/or chromatographic separation. The present invention provides a commercially viable process for the isolation and purification of chromones having desirable physiological activity.

The preparation of products for administration in pharmaceutical preparations may be performed by a variety of methods well known to those skilled in the art. The 7-hydroxychromones may be formulated as an herb powder in the form of their natural existence; as solvent and/or supercritical fluid extracts in different concentrations; as enriched and purified compounds through recrystallization, column separation, solvent partition, precipitation and other means, as a pure and/or a mixture containing substantially purified 7-hydroxychromones prepared by synthetic methods.

Various delivery systems are known in the art and can be used to administer the therapeutic compositions of the invention, e.g., aqueous solution, encapsulation in liposomes, microparticles, and microcapsules.

Therapeutic compositions of the invention may be administered parenterally by injection, although other effective administration forms, such as intraarticular injection, inhalant mists, orally and topically active formulations, transdermal iontophoresis or suppositories are also envisioned. One preferred carrier is physiological saline solution, but it is contemplated that other pharmaceutically acceptable carriers may also be used. In one preferred embodiment, it is envisioned that the carrier and 7-hydroxychromone(s) constitute a physiologically compatible, slow release formulation. The primary solvent in such a carrier may be either aqueous or non-aqueous in nature. In addition, the carrier may contain other pharmacologically acceptable excipients for modifying or maintaining the pH, osmolarity, viscosity, clarity, color, sterility, stability, rate of dissolution, or odor of the formulation. Similarly, the carrier may contain still other pharmacologically acceptable excipients for modifying or maintaining the stability, rate of dissolution, release or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, cream, gel, emulsion, solid, or dehydrated or lyophilized powder. Such formulations may be stored either in a ready to use form or requiring reconstitution immediately prior to administration. The manner of administering formulations containing the compositions for systemic delivery may be via subcutaneous, intramuscular, intravenous, topical, intranasal or vaginal or rectal suppository.

The amount of the composition that will be effective in the treatment of a particular disorder or condition will depend on the nature of the disorder of condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curves derived from in vitro or animal model test systems. For example, an effective amount of the composition of the invention is readily determined by administering graded doses of the composition and observing the desired effect.

The method of treatment according to this invention comprises administering internally or topically to a patient in need thereof a therapeutically effective amount of the individual and/or a mixture of 7-hydroxychromones from a single source or multiple sources. The purity of the individual and/or a mixture of 7-hydroxychromones includes, but is not limited to 0.01% to 100%, depending on the methodology used to obtain the compound(s). In a preferred embodiment doses of the 7-hydroxychrome and pharmaceutical compositions containing the same are an efficacious, nontoxic quantity generally selected from the range of 0.01 to 200 mg/kg of body weight. Persons skilled in the art using routine clinical testing are able to determine optimum doses for the particular ailment being treated.

This invention includes an improved method for isolating and purifying 7-hydroxychromones from plants. The improved method of this invention comprises: extraction of the ground biomass of a plant containing 7-hydroxychromone with single or combination of organic solvent and/or water; neutralization and concentration of the neutralized extract; and purification of said extract by polyamide or LH-20 chromatography. As provided above, these 7-hydroxychromones can be identified from the genera of numerous plant families. The method of this invention can be extended to the isolation of these compounds from any plant source containing these compounds.

Additionally the 7-hydroxychromones can be isolated from various parts of the plant including, but not limited to, the whole plant, stems, stem bark, twigs, tubers, flowers, fruit, roots, root barks, young shoots, seeds, rhizomes and aerial parts. In a preferred embodiment the 7-hydroxychromones are isolated from the whole leaves of *Aloe ferox*.

The following examples are provided for illustrative purposes only and are not intended to limit the scope of the invention.

EXAMPLES

Example 1

Preparation of Aloesin from the Exudates of *Aloe ferox*

A sample of aloesin was prepared using the methods described U.S. patent application Ser. No. 09/792,104, filed Feb. 26, 2001, entitled "Method of Purification of Aloesin," which is incorporated herein by reference in its entirety. Briefly, *Aloe* extract was isolated from the whole leaf of *Aloe ferox* that had been previously dissolved in hot water and filtered to remove undissolved particulates. The extract was then loaded onto a reverse phase column and aloesin was eluted from the column with 20-30% methanol.

Preparative HPLC
Column: IB SIL C18, 250 mm×4.6 mm, 5μ particle size
Mobile Phase: water/methanol gradient: 80%/20% (20 minutes); 40%/60% (10 minutes); 80%/20% (10 minutes)
Temperature: Ambient
Flow Rate: 1 mL/min
Detector Wavelength: 297
Sensitivity: 20
Product eluted between 8-9 minutes The compound was further purified by recrystalization to yield a light yellow solid with >95.2% purity.

Example 2

Preparation of Aloeresin A from the Exudates of *Aloe ferox*

A mixture of aloe exudates (35 kg) isolated from *Aloe ferox*, as described in U.S. patent application Ser. No. 09/792,104, filed Feb. 26, 2001, entitled "Method of Purification of Aloesin," which is incorporated herein by reference in its entirety, was added to hot water (200 L at 74° C.) and stirred for 1 hour. The solution was allowed to stand at room temperature for 2 days. The aqueous layer was decanted and the thick liquid residue was extracted again with hot water (200 L at 60° C.). A portion of this secondary extract (20 L) was concentrated and evaporated to dryness.

Dry extract (1.5 kg), containing 20.1% of aloeresin A, was dissolved in 25 L DI water. This solution was stirred for 30 minutes and loaded directly onto a pre-prepared polyamide column. The pre-prepared column (20 cm×100 cm) contained 20 L of polyamide and was cleaned with aqueous sodium hydroxide and then acidified with aqueous HCl. The column was then washed with DI water to neutral condition before the loading of the solution containing aloeresin A.

The load material was fed into the bottom of the column at about 1.5 L per minute keeping the pressure under 10 psi. The column was washed with water (20 L) followed by a methanol/water mixture (20 L 25% methanol). The column was blown dry using a peristaltic pump. Aloeresin A was then eluted with acetone (20 L). The eluent was collected, analyzed and evaporated to yield total of 377 g of a solid that contained 61.5% Aloeresin A.

Example 3

Purification of Aloeresin A by LH-20 Column Chromatography

A dry extract (9.6 g), containing approximately 45% of aloeresin A, was dissolved in 250 mL DI water. This solution was loaded directly onto a pre-prepared LH-20 column. The pre-prepared column (6.0 cm×12.0 cm) contained 400 mL of LH-20 resin and was equilibrated with 2 column volumes of DI water. The load material was fed into the top of the column and eluted with 800 mL 30% methanol followed by 600 mL of 100% methanol. The column was then equilibrated with 800 mL DI water and ready to be used again. A total of 38 fractions were collected with 50 mL in each fraction. Fractions 1-14 contained no compounds and were discarded. Fractions 15-30 were combined and evaporated to provide 1.43 g of anthraquinones in total solid of 4.615 g. The Aloeresin A was in fractions 31-36. These fractions were combined and evaporated to yield 4.05 g of Aloeresin A with a purity of 98%. The total solid recovery from the LH-20 column chromatography was 90.3%.

Example 4

Measurement of the Oxygen Radical Absorption Capacity (ORAC) of Aloeresin A and Aloesin The chromones, Aloesin and Aloeresin A, were tested for Oxygen Radical Absorption Capacity (ORAC) relative to green tea extract which contains more than 50% total catechins and more than 25% epigallocatechingallate (EGCG) and grape seed extract which contains more than 95% total phenols. The ORAC assay measures the time-dependent decrease in the fluorescence of β-phycoerythrin (β-PE) indicator protein, resulting from oxygen radical damage. This assay provides a quantitative measure of the total antioxidant capacity to protect the free radical sensitive β-phycoerythrin. Each reaction was calibrated using the known standard Trolox, a water soluble vitamin E analogue. The ORAC value refers to the net protection area under the quenching curve of β-phycoerythrin in the presence of an antioxidant. The results of the assay are reported on the basis of 1 ORAC unit equals 1 μM of Trolox. Aloeresin A (purity 76.0%), aloesin (95.2%), green tea extract and grape seed extract were dissolved in deionized water (5% solution W/V) and tested directly using the experimental procedures described in Cao et al. (1994) Free Radic. Biol. Med. 16:135-137 and Prior and Cao (1999) Proc. Soc. Exp. Biol. Med. 220:255-261. The results are set forth in the FIG. 4.

Example 5

Quantification of Fast and Slow Oxygen Radical Absorption Capacity (ORAC) for Aloeresin A and Aloesin The fast antioxidant activity is a measure of the net protection area under the quenching curve of β-phycoerythrin in the presence of an antioxidant, which completely inhibits free radical propagation, to the extent that 95% of β-phycoerythrin survives. Ascorbic acid, free phenolic compounds and thiol compounds are fast acting antioxidants. The slow antioxidant activity is a measure of the net protection area under the quenching curve of β-phycoerythrin in the presence of an antioxidant, which inhibits free radical propagation to the extent that 50% of β-phycoerythrin survives. Flavonoids, carotenoids and polyphenols are slow acting antioxidants. Aloeresin A (purity 76.0%), Aloesin (95.2%), green tea extract and grape seed extract, respectively were dissolved in deionized water (5% (W/V) solution) and tested directly using the experiment procedures described by Cao et al. (1994) Free Radic. Biol. Med. 16:135-137 and Prior and Cao (1999) Proc. Soc. Exp. Biol. Med. 220:255-261. The results are set forth in FIG. 5.

Example 6

Quantification of Lipid Peroxidation Inhibition Capacity (LPIC) of Aloeresin A Relative to Vitamin C and Alpha-Tocopherol Lipid Peroxidation Inhibition Capacity (LPIC) is a measure of the anti-oxidative ability of a sample to inhibit the initiation and propagation of a spontaneous lipid peroxidation reaction. Malonyldialdehyde (MDA) is one of the major by-products of lipid peroxidation and is commonly used as a means of measuring the extent of lipid peroxidation. MDA concentrations were measured using the thiobarbituric acid reaction. Aloeresin A (purity 76.0%), vitamin C and cc-tocopherol were dissolved in a phosphate-saline buffer at four different concentrations (5 mg/mL, 10 mg/mL, 25 mg/mL and 50 mg/mL) and then tested directly using the experiment procedures described by Stocks et al. (1974) Clinical Sci. Mol. 47:215-222 and Yu and Lee, U.S. Pat. No. 5,939,395. The results are set forth in FIG. 6.

Example 7

Improvement of Oxygen Radical Absorption Capacity (ORAC) for a Meta-Berry Drink Product by Addition of Aloeresin A A fruit drink product obtained from Oasis Wellness Network was determined, using the methods described in Example 3, to have an ORAC value of 3,129/oz. Aloeresin A, containing 76.0% aloeresin A was added to 40 mL of the drink (lot #0612, exp. November 2002) to produce a final concentration of 5 mg/mL and 15 mg/mL aloeresin A in the solution, respectively. These samples were then tested for whole ORAC value relative to the product in the absence of aloeresin A. using the experiment procedures illustrated described by Cao et al. (1994) Free Radic. Biol. Med. 16:135-137 and Prior and Cao (1999) Proc. Soc. Exp. Biol. Med. 220:255-261). The results are set forth in the FIG. 7.

Example 8

Figure 8:
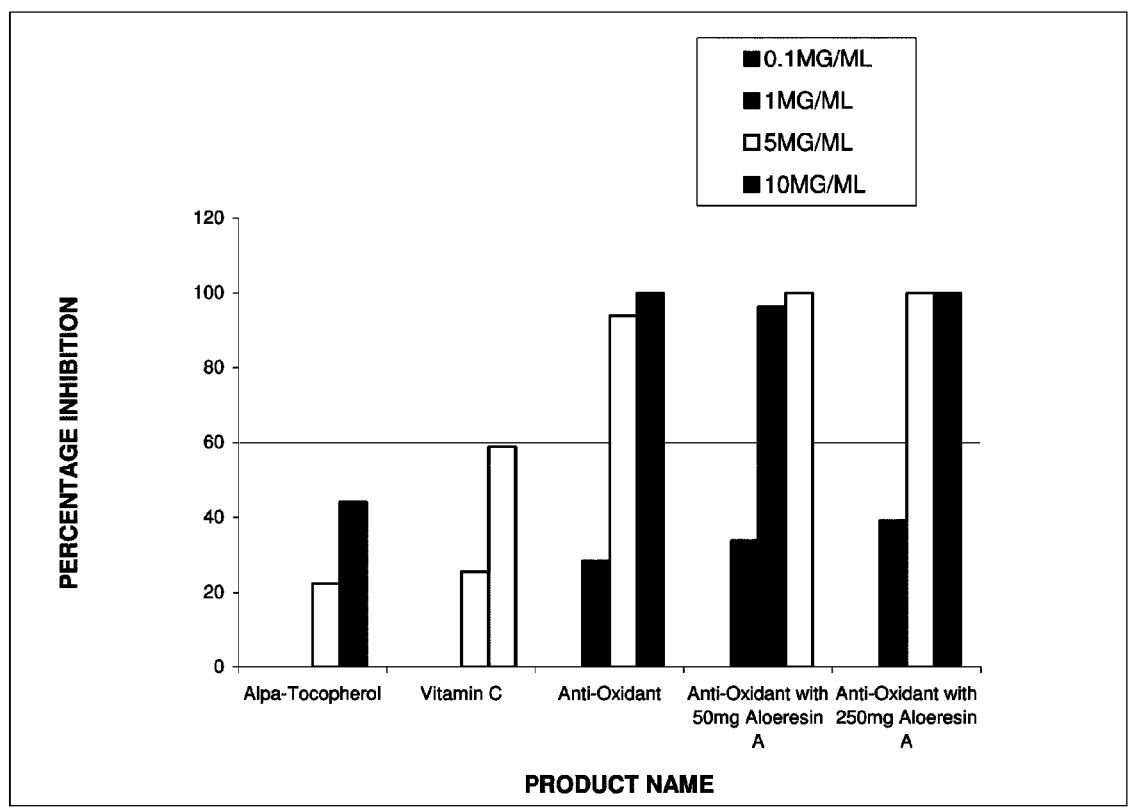
FIG. 8 depicts the improvement of lipid peroxidation inhibition capacity of an anti-oxidant formula upon the addition of Aloeresin A.

Improvement of Lipid Peroxidation Inhibition Capacity (LPIC) for an Anti-Oxidant Product by Addition of Aloeresin A An anti-oxidant product in a formulated tablet form obtained from Oasis Wellness Network was ground and mixed with a sample of aloeresin A (76.0% purity) in a final concentration equivalent to 50 mg/tablet and 250 mg/tablet, respectively. These samples were then tested for Lipid Peroxidation Inhibition Capacity (LPIC), as compared to the product absent aloeresin A, using the experiment procedures described by Stocks et al. (1974) Clinical Sci. Mol. 47:215-222 and Yu and Lee, U.S. Pat. No. 5,939,395. The test results are illustrated in the FIG. 8.

What is claimed is:

1. A method for treating ROS mediated diseases and conditions comprising administering to a host in need thereof an effective amount of a composition comprising a 7-hydroxychromone or a mixture of 7-hydroxychromones wherein said 7-hydroxychromone or a mixture thereof is selected from the group of compounds having the following structure:

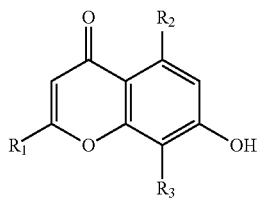

wherein
$R_1$ is an oxoalkyl or oxoalkenyl group;
$R_2$ and $R_3$ are independently selected from the group consisting of —H, —OH, alkyl, alkenyl, oxoalkyl, oxoalkenyl, hydroxylalkyl, hydroxylalkenyl, —OR, —SR, —NH$_2$, —NRH, —NR$_2$, —NR$_3^+$X$^-$, an ester selected from the group consisting of gallate, acetate, cinnamoyl and hydroxyl-cinnamoyl esters, trihydroxybenzoyl esters and caffeoyl esters; and a carbon, oxygen, nitrogen or sulfur glycoside of a single or a combination of multiple sugars selected from the group consisting of aldopentoses, methyl aldopentose, aldohexoses, ketohexoses;
wherein said alkyl and/or alkenyl group is a straight and/or branched chain having between 1-20 carbon atoms with and/or without double bonds in different positions;
X is selected from the group of pharmaceutically acceptable counter anions consisting of hydroxyl, chloride, iodide, sulfate, phosphate, acetate, fluorideand carbonate;
R is an alkyl group having between 1-20 carbon atoms and wherein the composition is comprised of 1% to 100% of said 7-hydroxychromones.

2. The method of claim 1 wherein said composition comprises a 7-hydroxychromone selected from aloesin or aloeresin A.

3. The method of claim 1 wherein said 7-hydroxychromone is obtained by organic synthesis.

4. The method of claim 1 wherein said 7-hydroxychromone is extracted from a plant or a plant part.

5. The method of claim 4 wherein said plant is selected from the group consisting of the genus of *Acacia, Adina, Aloe, Alternaria, Amoora, Antidesma, Artemisia, Baeckia, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces* and *Zonaria*.

6. The method of claim 4 wherein said plant is selected from the group consisting of *Acacia catechu, Acacia concinna, Aloe arborescens, Aloe barbadensis, Aloe cremnophila, Aloe ferox, Aloe saponaria, Aloe vera, Aloe vera* var. *chinensis, Antidesma membranaceum, Artemisia capillaries, Baeckia frutescens, Epimedium sagittatum, Garcinia dulcis, Hypericum japonicum, Polygonum cuspidatum, Sophora tomentosa*, and *Stephanitis rhododendri*.

7. The method of claim 4 wherein said plant part is selected from the group consisting of stems, stem barks, trunks, trunk barks, twigs, tubers, roots, root barks, young shoots, seeds, rhizomes, flowers and other reproductive organs, leaves and other aerial parts.

8. The method of claim 1 wherein the ROS mediated diseases and conditions are selected from the group consisting of atherosclerosis, coronary heart diseases, cataracts, dementia, Alzheimer's disease, cognitive dysfunction, diabetes mellitus, cancer, skin photo aging, skin wrinkles, sun burns, melanoma, and other degenerative processes associated with aging.

9. The method of claim 1 wherein the composition is administered in a dosage selected from 0.01 to 200 mg/kg of body weight.

10. The method of claim 1 wherein routes of the administration are selected from the group consisting of oral, topical, suppository, intravenous, and intradermic, intragaster, intramusclar, intraperitoneal and intravenous administration in an appropriate pharmaceutical formula.

11. The method of claim 1 wherein said composition comprises a 7-hydroxychromone wherein $R_2$ is alkyl; and $R_3$ is an ester selected from the group consisting of gallate, acetate, cinnamoyl and hydroxyl-cinnamoyl esters, trihydroxybenzoyl esters and caffeoyl esters; a carbon, oxygen, nitrogen or sulfur glycoside of a single or a combination of multiple sugars selected from the group consisting of aldopentoses, methyl aldopentose, aldohexoses, ketohexoses.

12. A method for providing an antioxidant to a host in need thereof, comprising administering to a host in need thereof an effective amount of a composition comprising a 7-hydroxychromone or a mixture of 7-hydroxychromones wherein said 7-hydroxychromone or a mixture thereof is selected from the group of compounds having the following structure:

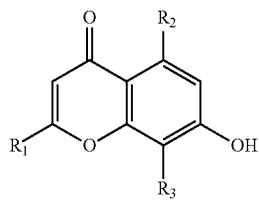

wherein
R$_1$ is an oxoalkyl or oxoalkenyl group;
R$_2$ and R$_3$ are independently selected from the group consisting of —H, —OH, alkyl, alkenyl, oxoalkyl, oxoalkenyl, hydroxylalkyl, hydroxylalkenyl, —OR, —SR, —NH$_2$, —NRH, —NR$_2$, —NR$_3^+$X$^-$, an ester selected from the group consisting of gallate, acetate, cinnamoyl and hydroxyl-cinnamoyl esters, trihydroxybenzoyl esters and caffeoyl esters; and a carbon, oxygen, nitrogen or sulfur glycoside of a single or a combination of multiple sugars selected from the group consisting of aldopentoses, methyl aldopentose, aldohexoses, ketohexoses;
wherein said alkyl and/or alkenyl group is a straight and/or branched chain having between 1-20 carbon atoms with and/or without double bonds in different positions;
X is selected from the group of pharmaceutically acceptable counter anions consisting of hydroxyl, chloride, iodide, sulfate, phosphate, acetate, fluorideand carbonate;
R is an alkyl group having between 1-20 carbon atoms and wherein the composition is comprised of 1% to 100% of said 7-hydroxychromones.

13. The method of claim 12 wherein said composition comprises a 7-hydroxychromone wherein R$_2$ is alkyl; and R$_3$ is an ester selected from the group consisting of gallate, acetate, cinnamoyl and hydroxyl-cinnamoyl esters, trihydroxybenzoyl esters and caffeoyl esters; a carbon, oxygen, nitrogen or sulfur glycoside of a single or a combination of multiple sugars selected from the group consisting of aldopentoses, methyl aldopentose, aldohexoses, ketohexoses.

14. The method of claim 13 wherein said composition comprises a 7-hydroxychromone selected from aloesin or and aloeresin A.

15. The method of claim 12 wherein said 7-hydroxychromone is obtained by organic synthesis.

16. The method of claim 12 wherein said 7-hydroxychromone is extracted from a plant or a plant part.

17. The method of claim 16 wherein said plant is selected from the group consisting of the genus of *Acacia, Adina, Aloe, Alternaria, Amoora, Antidesma, Artemisia, Baeckia, Cassia, Clusea, Cnidium, Convolvulus, Epimedium, Eriosema, Eriostemon, Eugenia, Garcinia, Hypericum, Lindenbergia, Pancratium, Penicillium, Polygonum, Ptaeroxylon, Rheum, Sophora, Stephanitis, Syzygium, Talaromyces* and *Zonaria*.

18. The method of claim 16 wherein said plant is selected from the group consisting of *Acacia catechu, Acacia concinna, Aloe arborescens, Aloe barbadensis, Aloe cremnophila, Aloe ferox, Aloe saponaria, Aloe vera, Aloe vera* var. *chinensis, Antidesma membranaceum, Artemisia capillaries, Baeckia frutescens, Epimedium sagittatum, Garcinia dulcis, Hypericum japonicum, Polygonum cuspidatum, Sophora tomentosa,* and *Stephanitis rhododendri*.

19. The method of claim 16 wherein plant part is selected from the group consisting of stems, stem barks, trunks, trunk barks, twigs, tubers, roots, root barks, young shoots, seeds, rhizomes, flowers and other reproductive organs, leaves and other aerial parts.

20. The method of claim 12 wherein the composition is administered in a dosage selected from 0.01 to 200 mg/kg of body weight.

21. The method of claim 12 wherein routes of the administration are selected from the group consisting of oral, topical, suppository, intravenous, and intradermic, intragaster, intramusclar, intraperitoneal and intravenous administration in an appropriate pharmaceutical formula.

* * * * *